United States Patent [19]

Semonsky et al.

[11] 4,005,090  
[45] Jan. 25, 1977

[54] 8-(β-AMINOETHYL)ERGOLINES-I

[75] Inventors: Miroslav Semonsky; Antonin Černý; Oldrich Nemecek; Karel Řezábek; Miroslav Seda; Vaclav Trcka; Jaroslava Grimová, all of Prague, Czechoslovakia

[73] Assignee: Spofa United Pharmaceutical Works, Prague, Czechoslovakia

[22] Filed: Mar. 19, 1975

[21] Appl. No.: 560,106

[30] Foreign Application Priority Data

Mar. 19, 1974   Czechoslovakia .......... 1971-74

[52] U.S. Cl. .......................... 260/285.5; 424/261
[51] Int. Cl.² ................................ C07D 457/02
[58] Field of Search ........................... 260/285.5

[56] References Cited

UNITED STATES PATENTS 3,557,118   1/1971   Arcamone et al. .......... 260/285.5
3,646,046   2/1972   Arcamone et al. .......... 260/285.5

OTHER PUBLICATIONS

Bernardi et al.; Gazz. Chem. Ital; vol. 24, pp. 936–978 (1964).
Morrison et al.; *Organic Chemistry* 2nd Edition; (1969) pp. 728, 741.
Bernardi et al.; *Chem. Abst.* vol. 60; 10739d, (1963).

Primary Examiner—R. Gallagher
Assistant Examiner—Mary C. Vaughn

[57]   ABSTRACT 8-(β-aminoethyl)ergolines-I of the general formula

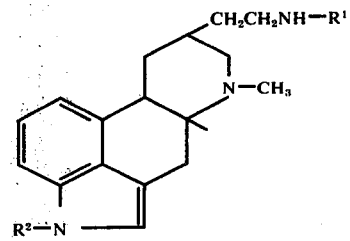

wherein $R^1$ is a hydrogen atom or an acyl group of the general formula $R^3$—CO, $R^3$ being a hydrogen atom, an alkyl group having from 1–5 carbon atoms, a phenyl group, a phenylalkyl group or a pyridyl group or substituents thereof, and $R^2$ is a hydrogen atom or a methyl group. Acid addition salts of the described ergolines evidence pharmacological activity in the anti-inflammation and hypotensive fields.

2 Claims, No Drawings

8-(β-AMINOETHYL)ERGOLINES-I

This invention relates to 8-(β-aminoethyl) ergoline-I compounds of the general formula (1)

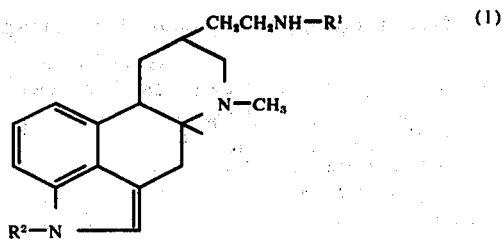

wherein $R^1$ is selected from the group consisting of a hydrogen atom and an acyl group of the general formula $R^3$—CO—, and $R^2$ is selected from the group consisting of a hydrogen atom and a methyl group, $R^3$ being selected from the group consisting of (a) a hydrogen atom, (b) an alkyl group having from 1–5 carbon atoms, a phenyl group, a phenylalkyl group, a pyridyl group, and mono, di and trisubstituted halogen derivatives thereof, alkoxy derivatives thereof having from 1–2 carbon atoms and methylene dioxy derivatives thereof.

The described compositions upon acidification yield addition salts which evidence pharmacological activity as hypotensive and anti-inflammatory agents. Studies have also revealed that the described compositions inhibit prolactive secretion in the adenohypophysis. Accordingly, these compositions are suitable for use in the preparation of medicaments, either alone or in combination with other known pharmacologically active compounds.

Acyl groups suitable for substitution in the generic formulation alluded to hereinabove include the following: acetyl, caproyl, benzoyl, p-toluyl, 2-, 3- or 4-chlorobenzoyl, 3,4-dichlorobenzoyl, 4-methoxybenzoyl, 3, 4, 5-trimethoxybenzoyl, 3,4-methylenedioxybenzoyl, phenylacetyl, 3, 4, 5-trimethoxyphenyl-acetyl, β-phenylpropionyl, nicotinoyl, isonicotinoyl, picolinoyl, 2-chloronicotinoyl and the like.

In accordance with the present invention 8-(β-aminoethyl)ergoline-I compounds and Nβ-acyl derivatives thereof may conveniently be prepared by reduction of D-6-methyl-8-cyanomethylergoline-I compounds of the general formula (2)

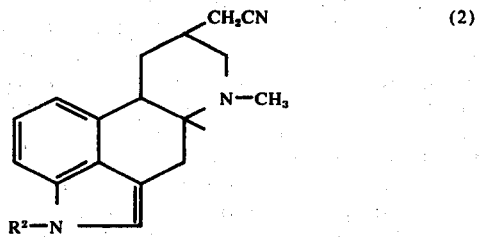

wherein $R^2$ is as represented above. The resultant D-6-methyl-8(β-aminoethyl)ergoline-I derivatives are then acylated, so yielding Nβ -acyl derivatives of general formula (1) wherein $R^1$, $R^2$ and $R^3$ are as represented above. As indicated, the compounds so obtained may be converted into pharmaceutically active compounds by reaction with organic or inorganic acids to yield the corresponding addition salts.

The D-6-methyl-8-cyanomethylergoline-I employed as a starting material for the preparation of the ergolines described herein is obtained in accordance with the well-known procedure described in U.K. Pat. No. 1,199,233. The D-1,6-dimethyl-8-cyanomethylergoline-I required by that technique is conveniently obtained by reaction of the D-6-methyl-8-cyanomethylergoline-I with methyl iodide in liquid ammonia and in the presence of potassium amide.

Reduction of the 8-cyanomethylergoline of formula (2) may be effected either by the use of complex metal hydrides or by means of catalytic hydrogenation.

The latter procedure, catalytic hydrogenation, may be effected in an inert solvent in a hydrogen ambient at pressures ranging from 20–100 atmospheres and at a temperature within the range of 20°–120° C and in the presence of a catalyst.

Solvents suitable for this purpose include methanol, ethanol, dioxane and mixtures thereof with water and ammonia. Catalysts employed in this use are platinum, palladium and Raney nickel, the latter being a preferred catalyst which is prepared by treating an aluminium-nickel alloy (40–50% nickel) with a 20% sodium hydroxide solution at temperatures ranging up to 20° C.

A typical catalytic hydrogenation process of the type discussed may conveniently be effected in the presence of Raney nickel using an 80% aqueous dioxane solvent saturated with ammonia at 0° C in a hydrogen ambient maintained within the range of 55–65 atmospheres and at a temperature within the range of 55–60° C. Hydrogenation under these conditions may be effected in about 2 hours.

Alternatively, the ergolines of formula (1) may be prepared by reacting carboxylic acids or their reactive derivatives with D-6-methyl-8-(β-aminoethyl)ergoline-I in the presence of condensing agents.

Acylation may be effected by reacting 8-β-aminoethylergoline with carboxylic acids in the presence of N,N'-dicyclohexylcarbodiimide or N,N'-carbonyl-bis-imidazole, or alternatively, by reacting azides, chlorides or anhydrides of carboxylic acids with an amino compound in the presence of a non-reactive base. Acylation may be conducted by treatment of the 8-(βaminoethyl)ergolines with chlorides of the carboxylic acids in a solvent at temperatures ranging from −10° C to +20° C in the presence of a tertiary base, as for example, pyridine or triethylamine. Suitable solvents for this reaction are inert organic compounds such as dichloromethane, chloroform, tetrachloromethane, benzene, ether, dioxane, dimethylformamide and the like or by the use of an excess of a tertiary organic base such as pyridine.

As noted above, pharmaceutically active addition salts of the described ergolines can be prepared by reacting them with organic or inorganic acids in a solvent, the ergoline being present in an amount of about 1 mol equivalent to 1–2 mol equivalents of acid. Acids suitable for this purpose are sulfuric, hydrochloric, hydrobromic, methanesulfonic, tartaric, maleic and the like, the solvents being selected from among methanol, ethanol, water and mixtures thereof.

The following examples are set forth for purposes of exposition and it will be understood by those skilled in the art that the invention is not restricted to the particular conditions, proportions or reagents set forth therein.

EXAMPLE 1

D-6-methyl-8(β-aminoethyl)ergoline-I

A suspension of D-6-methyl-8-cyanomethylergoline-I (5 grams) in 80% aqueous dioxane (200 ml) was saturated at 0–5° with gaseous ammonia. Next, an aqueous suspension of Raney nickel (approximately 10 g) was added and the mixture hydrogenated at 55°–60° C under 60 atm pressure of hydrogen in a rocking autoclave for 2 hours. After cooling, the catalyst was filtered off and washed with 80% aqueous ioxane. The combined colorless filtrates were then evaporated to dryness in the vacuum of a water pump and the residue crystallized from aqueous dioxane, so yielding D-6-methyl-8-(β-aminoethyl)ergoline-I as slightly yellowish needles, m.p. 175°–176° C; $[\alpha]_D^{20} = -71°$ (c = 0.5, ethanol).

EXAMPLE 2

D-6-methyl-8-(β-aminoethyl)ergoline-I bis (hydrogen maleate)

A solution of maleic acid (0.84 g) in ethanol (5 ml) was added to a solution of D-6-methyl-8-(β-aminoethyl)ergoline-I (0.93 g) in ethanol (25 ml) and the mixture allowed to crystallize overnight at approximately +5° C. Recrystallization of the separated salt from ethanol yields pure D-6-methyl-8-(β-aminoethyl)ergoline-I bis(hydrogen maleate) (1.42 g) as colorless needles, m.p. 162°–163° C; $[\alpha]_D^{20} = -34°$ (c = 0.5, water).

EXAMPLE 3

D-1,6-dimethyl-8-(β-aminoethyl)ergoline-I bis(hydrogen maleate)

To a suspension of D-1,6-dimethyl-8-cyanomethylergoline-I (1 g) in 80% aqueous methanol (40 ml), saturated at 0°–5° C with gaseous ammonia, was added an aqueous suspension of Raney nickel (about 2 g). The resultant mixture was hydrogenated under 65 atm pressure of hydrogen at 55°–60° C for 3 hours. The catalyst was filtered off and the solvents evaporated to dryness in vacuo, leaving about 1 g of almost colorless viscous base. This was dissolved in methanol (10 ml) and a solution of maleic acid (0.91 g) in methanol (2 ml) was added thereto. The mixture was then allowed to stand overnight. The separated salt (1.65 g), upon recrystallization from ethanol, yields pure D-1,6-dimethyl-8-(β-aminoethyl)ergoline-I bis(hydrogen maleate) as colorless needles, m.p. 150°–152° C; $[\alpha]_D^{20} = -37°$ (c = 0.5, water).

The starting D-1,6-dimethyl-8-cyanomethylergoline-I was prepared by the following procedure:

Potassium (0.165 g) was added to anhydrous liquid ammonia (500 ml) and transformed into potassium amide by addition of a catalytic amount of ferric nitrate. Into this reaction mixture was then introduced, under vigorous stirring, D-6-methyl-8-cyanomethylergoline-I (1.0 g), followed after 15 minutes of stirring by a solution of methyl iodide (0.70 g) in anhydrous ether (5 ml). The mixture was then stirred for 1 hour, the ammonia evaporated and the residue shaken between water and chloroform, containing 20% ethanol. The organic layer was dried over anhydrous sodium sulphate, the dying agent filtered off and the solvent evaporated under diminished pressure. The crude product (1.0 g) was purified first by chromatography on a silica gel column, using chloroform with 1–10% of ethanol as eluent, and then by recrystallization from an acetone-n-hexane mixture. D-1,6-dimethyl-8-cyanomethylergoline-I forms colorless needle-like crystals, m.p. 173°–175° C; $[\alpha]_D^{20} = -105°$ (c = 0.5, pyridine).

EXAMPLE 4

D-6-methyl-8-(β-acetylaminoethyl)ergoline-I

Acetic anhydride (0.12 g) was added to a stirred solution of D-6-methyl-8-(β-aminoethyl)ergoline-I (0.27 g) in pyridine (2.7 ml), the temperature of the mixture being kept at 0 to −2° C. The reaction mixture was recrystallized for 15 minutes at 0° C and for 1 hour at 20° C and then poured on ice (15 g). The pH of the mixture was adjusted to about 8 by addition of ammonia and the mixture allowed to stand for 2 hours at 5° C. The separated crude product (0.27 g) was filtered and chromatographed on a silica gel column, using a chloroform-ethanol mixture (9:1) as eluent. The resultant D-6-methyl-8-(β-acetylaminoethyl)ergoline-I was recrystallized from acetone, m.p. 198°–200° C; $[\alpha]_D^{20} = -98°$ (c = 0.5, pyridine).

EXAMPLE 5

D-6-methyl-8-(β-benzoylaminoethyl)ergoline-I

Pyridine (0.14 ml) was added to a solution of D-6-methyl-8-(β-aminoethyl)ergoline-I (0.404 g) in chloroform (16 ml). To this mixture, a solution of benzoyl chloride (0.23 g) in chloroform (2 ml) was added dropwise under stirring and cooling with ice. The reaction mixture, which deposits a solid, was stirred for 15 minutes at 0°–5° C and 1 hour at 20° C. Then, ethanol (4 ml) was added and the mixture shaken with dilute (1:10) ammonia and water. The chloroform solution was then dried under diminished pressure, yielding 0.56 g of crude D-6-methyl-8-(β-benzoylaminoethyl)ergoline-I which is purified first by chromotography on a silica gel column, using chloroform-ethanol (9:1) as eluent, and then by crystallization from methanol, m.p. 206°–208° C; $[\alpha]_D^{20} = -87°$ (c = 0.5, pyridine).

EXAMPLE 6

D-1,6-dimethyl-8-(β-nicotinoylaminoethyl)ergoline-I

Triethylamine (0.405 g) was added to a solution of D-1,6-dimethyl-8-(β-aminoethyl)ergoline-I (0.475 g) in chloroform (18 ml), and then nicotinoyl chloride hydrochloride (0.36 g) was introduced under stirring and cooling with ice and water. The reaction mixture was stirred for 15 minutes at 0°–5° C and for 2 hours at 20° C and then shaken with water. The chloroform portions were dried over sodium sulphate and dried in vacuo. The crude product (0.7 g) was purified first by chromatography on a silica gel column, using chloroform-ethanol (9:1) mixture as eluent, and then by crystallization from acetone. The thus-obtained D-1,6-dimethyl-8-(β-nicotinoylaminoethyl)eropoline-I forms almost colorless prisms, melting at 177°–178° C; $[\alpha]_D^{20} = -84°$ (c = 0.5 pyridine).

Using, e.g. p-chlorobenzoyl chloride, instead of nicotinoyl chloride hydrochloride, D-1,6-dimethyl-8-[β-(4-chlorobenzoyl)aminoethyl]ergoline-I, m.p. 205°–208° C (acetone); $[\alpha]_D^{20} = -92°$ (c = 0.5, pyridine) was obtained in a manner analogous to that described above.

What is claimed is:

1. D-6-methyl-8-(β-nicotinoylaminoethyl)ergoline-I.
2. D-1,6-dimethyl-8-(β-nictinoylaminoethyl)ergoline-I.

* * * *